(12) United States Patent
Landgrebe et al.

(10) Patent No.: US 6,248,733 B1
(45) Date of Patent: Jun. 19, 2001

(54) METHOD FOR LIMITING THE GROWTH OF MICROORGANISMS USING METAL-CONTAINING COMPOUNDS

(75) Inventors: Kevin D. Landgrebe, Woodbury; Charles E. Shelburne, Brooklyn Park; Terrance P. Smith, Woodbury, all of MN (US); Gregory D. Cuny, Hudson, MA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/004,892

(22) Filed: Jan. 9, 1998

(51) Int. Cl.$^7$ ....................... C07D 229/00; C07D 205/12
(52) U.S. Cl. ............................ 514/184; 540/202; 540/203
(58) Field of Search .................... 546/2; 514/184; 510/161, 179, 199, 292, 180; 540/202, 203

(56) References Cited

U.S. PATENT DOCUMENTS

| | | | |
|---|---|---|---|
| 4,775,625 | 10/1988 | Sieber | 435/238 |
| 4,885,366 | 12/1989 | Gunter et al. | 544/300 |
| 4,906,750 | 3/1990 | Gunther et al. | 544/300 |
| 4,915,683 | 4/1990 | Sieber | 604/4 |
| 4,937,344 | 6/1990 | Gunther et al. | 544/300 |
| 5,149,718 | 9/1992 | Meruelo et al. | 514/732 |
| 5,166,326 | 11/1992 | Smith et al. | 534/701 |
| 5,180,705 | 1/1993 | Smith et al. | 503/227 |
| 5,208,336 | 5/1993 | Gunther et al. | 544/300 |
| 5,314,998 | 5/1994 | Smith et al. | 534/701 |
| 5,326,788 | 7/1994 | Meruelo et al. | 544/732 |
| 5,418,130 | 5/1995 | Platz et al. | 435/2 |
| 5,571,666 | 11/1996 | Floyd et al. | 435/2 |
| 5,650,441 | 7/1997 | Aszalos et al. | 514/397 |

FOREIGN PATENT DOCUMENTS

| | | | |
|---|---|---|---|
| 457 196 A2 | 11/1991 | (EP) . | |
| 0 503 780 A1 | 9/1992 | (EP) . | |
| 0 503 708 * | 9/1992 | (EP) | C09B/69/10 |
| 0 508 573 A1 | 10/1992 | (EP) . | |
| 0 591 016 A1 | 4/1994 | (EP) . | |
| WO 90/13296 | 11/1990 | (WO) . | |
| WO 92/22610 | 12/1992 | (WO) . | |
| WO 93/00815 | 1/1993 | (WO) . | |
| WO 95/02325 | 1/1995 | (WO) . | |
| WO 95/16348 | 6/1995 | (WO) . | |
| WO 98/03224 | 1/1998 | (WO) . | |
| WO 98/20904 | 5/1998 | (WO) . | |

OTHER PUBLICATIONS

Gupta et al, Spectral, Microbial studies, Proc. Natl. Acad. Sci., India, Sect A, 61(3),285–92, 1991.*
Motschi et al, The trans–influence in Pt(II) complexes. Helv. Chim. Acta, vol. 63 No. 7, 2071–86, 1980.*
Wade, *Organic Chemistry*(3$^{rd}$ Edition), Chapter 16, pp. 730–732, Prentice Hall Inc., (1995).
Wade, *Organic Chemistry*(3rd Edition), Chapter 16, pp. 730–732, Prentice Hall Inc., (1995).
Database WPI: Derwent Publications Ltd., London, GB; AN 93–252660, XP002078829, Dainippon, "Lower Toxicity Anti–HIV Drug—Comprises Azo Dyes with Acid Function Group Effect Ingredient," p. 5, line 10—p. 7, line 28 & JP 05 170646 A—Abstract.
Database WPI: Derwent Publications Ltd., London GB; AN 77–28568Y, XP002078830, Mosc Textile Inst., "Fungicide Azo Dye Preparation Hydroxy Quinoline Diazotise Amine Textile," abstract & SU 486 682 A.–Abstract.
Database WPI: Derwent Publication Ltd., London, GB; AN 77285684Y, XP002078831, Mosc Textile Inst., "Antimicrobial Azo Dye Produce Couple Diazo Compound Salicylanilide Halo Derivative Textile Finish,"abstract & SU 401 169 A.
Article: Abildgaard et al., "Assignment of the Ligating Nitrogen in o,o'–Dihydroxyazoarene Complexes of Nickel–, Palladium–, and Platinum(ii) by $^1$H and $^{13}$C NMR Spectroscopy," *Inorg. Chem.*, vol. 33, No. 23, 1994, pp. 5271–5277.
Z. Jackson et al., "Killing of Candida Albicans by Antibody–targeted photolysis", Abstract No. F–104, Interscience Conference on Antimicrobial Agents & Chemotherapy, Sep. 28–Oct. 1, 1997, Toronto, Ontario, Canada.

(List continued on next page.)

*Primary Examiner*—Jose' G. Dees
*Assistant Examiner*—Alton Pryor
(74) *Attorney, Agent, or Firm*—James A. Rogers

(57) ABSTRACT

This invention relates to the use of compounds having the general structure:

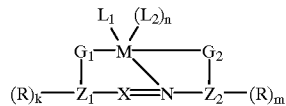

wherein: Z1 and Z2 each independently represent an arene nucleus, which has from 5 to 14 ring atoms; G1 and G2 each independently represent a metal ligating group; R represents a hydrogen atom, a halogen atom, an alkyl group, an acylamino group, an alkoxy group, a sulfonamido group, an aryl group, a thiol group, an alkylthio group, an arylthio group, an alkylamino group, an arylamino group, an amino group, an alkoxycarbonyl group, an acyloxy group, a nitro group, a cyano group, an alkylsulfonyl group, an arylsulfonyl group, an alkylsulfoxyl group, an arylsulfoxyl group, an aryloxyl group, a hydroxyl group, a thioamido group, a carbamoyl group, a suffamoyl group, a formyl group, an acyl group, a ureido group, an aryloxycarbonyl group, a silyl group, or a sulfoalkoxy group; L1 represents a nitrogen heterocycle; L2 represents a monodentate or polydentate (e.g., bidentate) ligand; X represents nitrogen or a methine (CH) group; M is a divalent or polyvalent transition metal ion where the coordination number is at least 4; and k, m, and n are whole numbers less than or equal to 3 as antimicrobial agents to inhibit the growth or replication of microorganisms such as viruses, bacteria, and fungi.

42 Claims, No Drawings

OTHER PUBLICATIONS

M. Bhatti et al., "An Investigation Into the Mechanisms Involved In, and Possible Targets of, Lethal Photosensitisation of Porphyromonas Gingivalis", Abstract No. B–94, Interscience Conference on Antimicrobial Agents & Chemotherapy, Sep. 28–Oct. 1, 1997, Toronto, Ontario, Canada.

S. Gaspard, et al., "Studies on photoinactivation by various phthahlocyanines of a free or replicating non–enveloped virus," *Journal of Photochemistry and Photobiology B: Biology* 31 (1995) pp. 159–162.

B. Henderson et al., p. 98 from *Photodynamic Therapy: Basic Principles and Clincal Applications* (1992).

H. Okamoto et al., "Dye–Mediated Bacterial Effect of He–Ne Laser Irradiation on Oral Microorganisms," *Lasers in Surgery and Medicine* 12:450–458 (1992).

R. Pal et al., "Effect of Evans Blue and Trypan Blue on Syncytia Formation and Infectivity of Human Immunodeficiency Virus Type I and Type II In Vitro," *Aids Research and Human Retroviruses*, vol. 7, No. 6, (1991).

Motschi et al., *Helvetica Chimica Acta*, *63*(7):2071–2086 (1980).

\* cited by examiner

METHOD FOR LIMITING THE GROWTH OF MICROORGANISMS USING METAL-CONTAINING COMPOUNDS

FIELD OF THE INVENTION

This invention relates to the field of microbiology, and in particular to a method for inactivating viruses and/or limiting the growth of bacteria and fungi.

BACKGROUND OF THE INVENTION

Viruses are small (about 20–300 nanometer (nm) in diameter) obligate parasites that can infect unicellular organisms such as bacteria, and all higher plants and animals. The viral core contains either single-stranded or double-stranded DNA or RNA and is surrounded by a protein coat. Enveloped viruses are additionally surrounded by a glycoprotein-studded cell-derived lipid membrane. Viruses cause diseases in animals and humans. Destruction of virus and/or virus-infected cells prevents and/or reduces the physiologic alterations produced in the host resulting from the disease processes associated with viral infection.

Bacteria are prokaryotic unicellular microorganisms. Bacteria occur in three basic structural forms; rods (bacilli), spheres (cocci), and spirals (spirilla). An additional higher order structure is denoted by the prefixes staph, diplo, and strepto, as in staphylococci bacteria, indicating that the individual spheres are bunched together in grape-like clusters, in diplococci, indicating paired cocci, and in streptobacilli, where the rods are associated into chain-like structures. Bacteria colonize cell surfaces causing infection and are capable of replication in both aerobic and anaerobic locations in the body.

Fungi are eukaryotic organisms that comprise the yeasts, which are unicellular, and the molds, which are multicellular organisms. Fungi can also cause disease and produce pathogenic sequelae.

Viruses, bacteria and fungi spread through a variety of means with particular routes of dissemination more common to some viruses or some bacteria or fungi than to others. For example, viruses, bacteria and fungi spread through physical contact or exposure to an infected source, such as contact or exposure to a living organism infected with a particular virus, bacterium or fungus. Spread of viruses, bacteria and fungi can also occur through an intermediary such as air, water or surfaces. Viruses, bacteria and fungi pass from one host to another and the pathogenic sequelae associated with a particular virus or a particular bacterium or fungus is a function of the microorganism and a function of the ability of the particular host to be infected or to support replication of that microorganism.

Microorganisms can be killed or rendered static by a number of physical and chemical methods. Physical methods include heat and radiation. For example, oxidation of bacterial proteins and desiccation of the cytoplasm occurs using dry heat for 2 hours at 160° C. Treatment with moist heat at 100° C. for 2 hours causes denaturing of proteins. Radiation (ultraviolet or ionizing radiation) can denature DNA of bacteria and fungi and the nucleic acids (either DNA or RNA) of viruses, thereby limiting their replication in a suitable host.

There are a number of chemicals that have been used to limit viral, fungal and bacterial growth. Alcohols (usually as 70% aqueous ethyl or isopropyl alcohol) act as protein denaturants in bacteria and destroy the lipid bilayer of enveloped viruses. Phenol (carbolic acid) and phenol derivatives such as hexachlorophene denature proteins in bacteria and in viral capsids. Formaldehyde (also glutaraldehyde) reacts with the amino substituents of nucleotide bases and crosslinks DNA and RNA in viruses and DNA in bacteria and fungi. Ethylene oxide gas alkylates amino groups in viruses and bacteria and is used for disinfecting dry surfaces. Ether destroys the lipid envelope of enveloped viruses. Non-enveloped viruses are not susceptible to inactivation by ether. Detergents also are good inactivators of enveloped viruses and kill bacteria by disrupting the cell membrane. Chlorhexidine gluconate disrupts the membranes of bacteria, fungi and viruses and thus displays broad antimicrobial activity.

Heavy metals such as silver, copper, and mercury are virucides and bactericides by virtue of their ability to combine with sulfhydryl groups in proteins. Mercurochrome is an organic compound of mercury that is safer than elemental mercury for use on skin, but mercurochrome is rapidly inactivated by contaminating residual organic compounds on skin that has not been sufficiently cleaned. Oxidizing agents such as hydrogen peroxide, iodine, hypochlorite, and chlorine oxidize sulfhydryl groups and are also capable of limiting microorganism growth.

A number of antiviral agents are known. These include amantadine (which blocks uncoating of virus particles in Influenza virus, type A) as well as a variety of nucleoside analogs that interfere with nucleic acid synthesis. Examples of nucleoside analogs include AZT, acyclovir, ganciclovir, and vidarabine. These drugs require virus replication for inactivation. Nucleoside analogs can cause adverse side effects because they also interfere with nucleic acid synthesis in cells of the host. Many are not effective over extended times because as viruses replicate they mutate in ways that render the drugs ineffective.

Antibiotics have traditionally been defined as chemicals made by microorganisms that kill bacteria. Except for the antibiotic rifampin, which has a mode of action in viruses that is different from its mechanism of killing bacteria, antibiotics generally have no effect on viruses. Bacitracin, the ceplialosporins, cycloserine, the penicillins, and vancomycin are all antibiotics that lead to the destruction or cessation of growing bacterial cells by inhibition of cell wall synthesis. The cephalosporins and penicillins are β-lactams, cycloserine is an isoxazolidineone, and vancomycin is a glycopeptide. Antibiotics that interfere with cell membrane function include the polyenes (such as amphotericin B) and the polymyxins.

Chloramphenicol, the erythromycins, the tetracyclines and the aminoglycosides (such as streptomycin, neomycin, and gentamycin) bind to bacterial ribosomes and inhibit protein synthesis. Chloramphenicol is mainly bacteriostatic, so bacterial growth resumes after the drug is withdrawn. The erthyromycins are macrolide ring structures containing pendant amino sugar moieties. The tetracyclines are composed of four linearly-fused rings. Sulfonamides act by entering into the synthetic pathway for folic acid (and eventually the nucleic acids) in place of p-aminobenzoic acid (PABA). The chemical structure of the sulfonamides is similar to PABA. Another drug that inhibits nucleic acid synthesis is rifampin, which inhibits RNA polymerase in bacteria, thus preventing synthesis of mRNA. Resistance to antibiotics is common and can result either from mutations in the chromosomal DNA at a locus that controls susceptibility to a certain drug, or it may arise from extrachromosomal (e.g., plasmid) DNA that encodes enzymes that destroy the drug.

The potential for the presence of pathogenic bacteria, viruses and fungi in biological fluids such as saliva, tears, blood, and lymph is of major concern to health care workers and patients. Surfaces contaminated with bacteria, viruses and fungi can facilitate spread of infections. For this reason, methods for minimizing the transmission of pathogens in the home, in hospitals, and in daycare centers is important. Additionally, the usefulness of valuable food and industrial products can be destroyed by the presence of bacteria and viruses. Many antimicrobial agents are too toxic, too costly or otherwise impractical as routine disinfecting compounds. Some antimicrobial agents are unstable and become inactive over time or the microorganism develops resistance to the antimicrobial agent. As a result, there is a need for a simple, alternative, effective method for inactivating viruses and limiting bacterial and fungal growth.

International Patent Application No. WO 95/16348 discloses a method for inactivating viruses in body fluids that involves passing the body fluid through a column containing an "inactivating agent" such as charcoal or various dyes.

Photoinactivation of viruses has been described in some systems. U.S. Pat. No. 5,418,130 discloses photoinactivation of viruses in blood employing derivatives of porphyrin and psoralen. U.S. Pat. No. 4,775,625 discloses a continuous flow device for the inactivation of viruses using a combination of merocyanine dye and light. Most reports discussing virus inactivation using a combination of dyes and light limit the use of the dyes and light to the inactivation of enveloped viruses with one exception. Human rhinovirus type 5 (RV-5), a non-enveloped picornavirus, was inactivated by irradiation in the presence of a phthalocyanine dye (*J. Pholochem. Photobiol. B*. (Switzerland), 31; (3); 159–62, December 1995).

Photosensitization of bacteria has also been described in some systems. For example, Malik et. al. (*Photodynamic Therapy: basic principles and clinical applications*, edited by Narbara W. Henderson and Thomas J. Dougherty, published by Marcel Dekker, Inc., p. 98, 1992) described susceptibility of gram-positive bacteria, but the resistance of gram-negative bacteria, to photosensitization by hematoporphyrin. Minnock et. al (*J. Photochem. and Photobiol*. 32:159–164, 1996) described the use of a water soluble zinc phthalocyanine dye and light to kill gram-positive and gram-negative bacteria. Okamoto et. al (*Las. Surg. Med*., 12: 450–458, 1992) described the bactericidal effect of light in combination with thiazines, oxazines, xanthenes, acridines, phenazines or phenylmethane dyes on *S. sobrinus*. Azo dyes were ineffective at killing *S. sobrinus* in their study.

Some azo dyes have been used to inactivate viruses and bacteria. International Patent Application No. WO 92/22610 discloses bisazo dyes for non-photoinduced inactivation of viruses. Additionally, Pal et al. (*AIDS Res. Hu. Retroviruses*, 7(6): 537–543, 1991) have demonstrated the inhibition of infectivity in vitro of CD4 cells by HIV-1 in the presence of Evans Blue or Trypan Blue using non-photoinduced methods. New photo-inducible compounds are needed and, in particular, there remains a need for new antimicrobial compounds and methods that can inhibit growth of more than one type or family of microorganism.

SUMMARY OF THE INVENTION

Therefore according to the present invention there is provided a method for limiting the growth and/or the presence of a virus, bacterium and fungus including the step of contacting the virus, bacterium or fungus with a metal-containing compound, having the following formula:

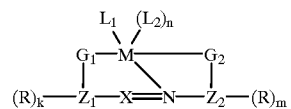

wherein:
Z1 and Z2 each independently represent an arene nucleus, having from 5 to 14 ring atoms;

G1 and G2 each independently represent a metal ligating group, wherein G1 and G2 may be contained within or pendant from at least one of Z1 and Z2;

R represents a hydrogen atom, a halogen atom, an alkyl group, an acylamino group, an alkoxy group, a sulfonamido group, an aryl group, a thiol group, an alkylthio group, an arylthio group, an alkylamino group, an arylamino group, an amino group, an alkoxycarbonyl group, an acyloxy group, a nitro group, a cyano group, an alkylsulfonyl group, an arylsulfonyl group, an alkylsulfoxyl group, an arylsulfoxyl group, an aryloxyl group, a hydroxyl group, a thioamido group, a carbamoyl group, a sulfamoyl group, a formyl group, an acyl group, a ureido group, an aryloxycarbonyl group, a silyl group, or a sulfoalkoxy group;

L1 represents a nitrogen heterocycle, substituted with R1 or R2 or both R1 and R2;

R1 and R2 each independently represent a hydrogen, a halogen atom (such as an iodine, chlorine or bromine atom), an alkyl group, including vinyl groups, hydroxyalkyl groups, and the like, an acylamino group, an alkoxy group, a sulfonamido group, an aryl group, an alkylthio group, an alkylamino group, an alkoxycarbonyl group, an acyloxy group, an alylsulfonyl group, an alkylsulfoxyl group, an alkylcarbamoyl group, an alkylsulfamoyl group, a formyl group, an acyl group, a silyl group, or a sulfoalkoxy group;

L2 represents a monodentate or polydentate (e.g., bidentate) ligand;

X represents nitrogen or a methine (CH) group;

M is a divalent or polyvalent transition metal ion where the coordination number is at least 4;

and k, m, and n are whole numbers less than or equal to 3.

In one embodiment of this invention, the method further comprises exposing the combination to light and in another embodiment n is a whole number less than or equal to 2.

Where the term "group" or "nucleus" is used in describing substituents, substitution is anticipated on the substituent. For example, "alkyl group" includes vinyl groups, ether groups (e.g., CH₃—CH₂—CH₂—O—CH₂—), haloalkyls, nitroalkyls, carboxyalkyls, hydroxyalkyls, etc. Similarly, the term "arene nucleus" refers, for example, to not only phenyl, but to chlorophenyl, ethylphenyl, and naphthyl as well.

In one embodiment of this aspect of the invention, the method further comprises the step of exposing the composition to light for at least one time. In one embodiment, the metal-containing compound is compound 1 and preferably the metal-containing compound is selected from the group consisting of compound

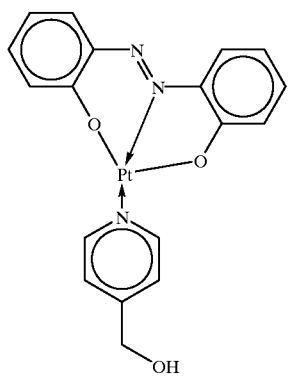

1B

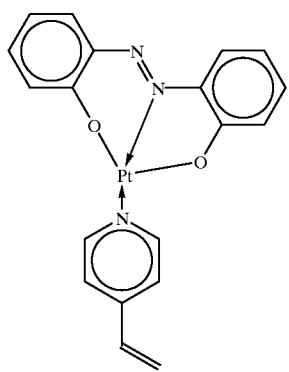

1A

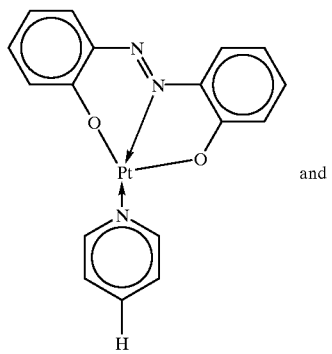

1H and

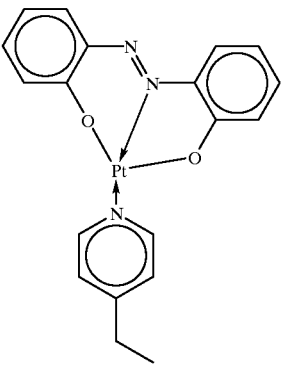

1F

-continued

In one embodiment, the microorganism is a virus, for example, an enveloped virus such as HIV, a member of the Herpesvirus group, or an Influenza virus. In another embodiment, the microorganism is a bacterium such as a gram-positive bacterium or a gram-negative bacterium. In yet another embodiment, the microorganism is a fungus, in one example a yeast.

In a preferred embodiment of this method, the contacting step further comprises contacting a surface with the composition. In one embodiment, the composition of the contacting step comprises the metal-containing compound in a liquid, or the composition can be added to a liquid. In another embodiment, the contacting step further comprises adding the metal-containing compound to a solid.

In a preferred embodiment, replication of the microorganism is inhibited by the contacting step or the microorganism is killed by the contacting step. The metal-containing compound is in either a liquid or a solid form during the contacting step. The composition used in the method of this invention can include at least one other antimicrobial compound.

In one embodiment, the metal-containing compound on a surface or in a liquid is exposed to light more than once.

This invention further relates to a method for disinfecting a surface comprising the step of applying a composition comprising a metal-containing compound to a surface, the metal-containing compound having the general structure:

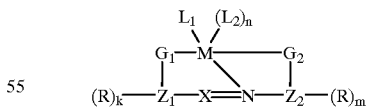

wherein:

Z1 and Z2 each independently represent an arene nucleus, having from 5 to 14 ring atoms;

G1 and G2 each independently represent a metal ligating group, wherein G1 and G2 may be contained within or pendant from at least one of Z1 and Z2;

R represents a hydrogen atom, a halogen atom, an alkyl group, an acylamino group, an alkoxy group, a sulfonamido group, an aryl group, a thiol group, an alkylthio group, an arylthio group, an alkylamino group, an arylamino group, an amino group, an alkoxycarbonyl group, an acyloxy group, a nitro group, a cyano group, an alkylsulfonyl group, an arylsulfonyl group, an alkylsulfoxyl group, an arylsulfoxyl group, an aryloxyl group, a hydroxyl group, a thioamido group, a carbamoyl group, a sulfamoyl group, a formyl group, an acyl group, a ureido group, an aryloxycarbonyl group, a silyl group, or a sulfoalkoxy group;

L1 represents a nitrogen heterocycle, substituted with R1 or R2 or both R1 and R2;

R1 and R2 each independently represent a hydrogen, a halogen atom, an alkyl group, including vinyl groups, hydroxyalkyl groups, and the like, an acylamino group, an alkoxy group, a sulfonamido group, an aryl group, an alkylthio group, an alkylamino group, an alkoxycarbonyl group, an acyloxy group, an alylsulfonyl group, an alkylsulfoxyl group, an alkylcarbamoyl group, an alkylsulfamoyl group, a formyl group, an acyl group, a silyl group, or a sulfoalkoxy group;

L2 represents a monodentate or polydentate (e.g., bidentate) ligand;

X represents nitrogen or a methine (CH) group;

M is a divalent or polyvalent transition metal ion where the coordination number is at least 4; and k, m, and n are whole numbers less than or equal to 3.

In a preferred method, the method additionally includes exposing the surface to light. In yet another aspect of this embodiment, the composition further comprises another antimicrobial agent.

The invention also relates to a composition comprising a first antimicrobial agent comprising a metal-containing compound having the general structure:

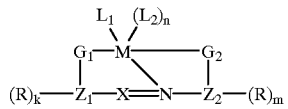

wherein:

Z1 and Z2 each independently represent an arene nucleus, having from 5 to 14 ring atoms;

G1 and G2 each independently represent a metal ligating group, wherein G1 and G2 may be contained within or pendant from at least one of Z1 and Z2;

R represents a hydrogen atom, a halogen atom, an alkyl group, an acylamino group, an alkoxy group, a sulfonamido group, an aryl group, a thiol group, an alkylthio group, an arylthio group, an alkylamino group, an arylamino group, an amino group, an alkoxycarbonyl group, an acyloxy group, a nitro group, a cyano group, an alkylsulfonyl group, an arylsulfonyl group, an alkylsulfoxyl group, an arylsulfoxyl group, an aryloxyl group, a hydroxyl group, a thioamido group, a carbamoyl group, a sulfamoyl group, a formyl group, an acyl group, a ureido group, an aryloxycarbonyl group, a silyl group, or a sulfoalkoxy group;

L1 represents a nitrogen heterocycle, substituted with R1 or R2 or both R1 and R2;

R1 and R2 each independently represent a hydrogen, a halogen atom, an alkyl group, including vinyl groups, hydroxyalkyl groups, and the like, an acylamino group, an alkoxy group, a sulfonamido group, an aryl group, an alkylthio group, an alkylamino group, an alkoxycarbonyl group, an acyloxy group, an alylsulfonyl group, an alkylsulfoxyl group, an alkylcarbamoyl group, an alkylsulfamoyl group, a formyl group, an acyl group, a silyl group, or a sulfoalkoxy group;

L2 represents a monodentate or polydentate (e.g., bidentate) ligand;

X represents nitrogen or a methine group;

M is a divalent or polyvalent transition metal ion where the coordination number is at least 4; and k, m, and n are whole numbers less than or equal to 3, and a second antimicrobial agent. In one embodiment the second antimicrobial agent is selected from the group consisting of an antiviral agent, an antibacterial agent and an antifungal agent.

In another aspect of this invention, the invention relates to a method for limiting the growth and/or presence of a virus, bacterium and/or fungus including the step of contacting the virus, bacterium and/or fungus with a metal-containing compound having the following formula:

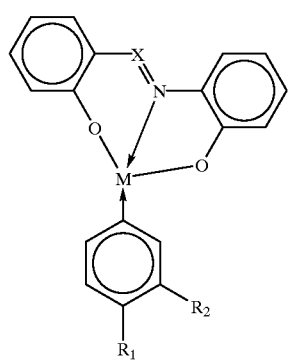

wherein R1 and R2 are each independently selected from the group consisting of H, $CH_2OH$, $CH=CH_2$ and $CH_2CH_3$, X is a methine (CH) group, and M is Pt. In a preferred embodiment at least one of R1 or R2 is H.

In another aspect of this invention, the invention relates to a metal-containing compound having the general structure:

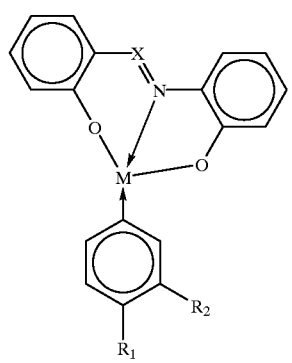

wherein R1 is $CH_2OH$ or $CH_2CH_3$, R2 is H, X is a methine (CH) group, and M is Pt.

DETAILED DESCRIPTION OF THE INVENTION

For the purposes of this invention, the terms "inhibition of virus" and "virucidal activity" as used herein refer to a reduction in the amount of virus present in a sample contacted with the metal-containing compounds of this invention. In one embodiment, the terms refer to at least a 50% reduction in the amount of virus detected and preferably at least a 75% reduction in the amount of virus detected on or within surfaces, substances or products treated according to the methods of this invention.

For the purposes of this invention, the language "limiting the growth and/or the presence of a virus, bacterium and fungus" as used herein refers to methods that employ the use of the compounds described in this invention to inhibit, kill, prevent the replication of or reduce the number of viruses, bacteria or fungi present on a surface, substance or product exposed to the compounds described in this invention. For experimental purposes, growth of bacteria or fungi is limited when a particular bacterium or fungus is growth inhibited or killed when exposed to the compounds of this invention. For example, growth of bacteria or fungi is limited by the compounds of this invention when disks moistened with a solution containing the compounds of this invention create visible zones of growth inhibition on a surface containing the bacteria or fungi.

The term "contacting" as used in the methods of this invention includes either physical contact of the compounds of this invention with a virus, a bacterium or a fungus or exposure of a virus, a bacterium or a fungus to the compounds of this invention. Without intending to limit the scope of this invention, some of the compounds of this invention may form diffusible substances, such as singlet oxygen that mediates an antimicrobial effect on the virus, bacterium or fungus. Therefore, physical contact may not be necessary.

The antimicrobial properties of some of the compounds of this invention are enhanced when the compounds are exposed to light. Under conditions where oxygen concentration is high and there are no reducing agents present, singlet oxygen can be a microbial inhibitory agent. Singlet oxygen reacts with amino acids, nucleotides, and the double bonds of fatty acids in lipid membranes. The production of singlet oxygen from triplet oxygen involves regeneration of the ground-state compound. While not intending to limit the scope of the present invention and although the mechanism of action of the compounds of the present invention in inhibiting growth of bacteria, viruses, and fungi has not been fully elucidated, the currently available data are compatible with the metal-containing compounds of this invention acting as a catalyst (i.e., metal-containing compounds are not consumed) in the formation of reactive species, such as singlet oxygen, to cause destruction of microorganisms. Regardless of the mechanism involved, the metal-containing compounds used in the methods of this invention are able to inhibit virus growth and to inhibit the growth of bacteria and fungi. Advantageously, the photosensitive metal-containing compounds are recyclable as antimicrobial agents. That is, preferably their antimicrobial activity is enhanced during light exposure and the antimicrobial activity can be reinitiated during reexposure to light.

The term "bacteristatic" refers herein to the property of inhibiting bacterial growth but not necessarily killing the bacteria. A "bactericide" kills bacteria. A fungi-stat inhibits replication of a fungus while a fungicide kills the fungus. The compounds of this invention can be either bacteriostatic or bactericidal, fungi-static or fungicidal. Methods for limiting the growth and/or the presence of a bacterium and fungus includes "static" (i.e., inhibiting) and "cidal" (i.e., killing) activities.

The invention provides a method for limiting the growth and/or the presence of a virus, a bacterium or fungus to prevent their colonization, infection and/or replication in a host. The method includes contacting the virus, bacterium or fungus with a metal-containing compound having the following formula:

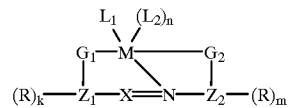

wherein:

Z1 and Z2 each independently represent an arene nucleus, which has from 5 to 14 ring atoms;

G1 and G2 each independently represent a metal ligating group, (e.g., oxygen, sulfur, amines, substituted amines, acylamido, sulfonamido), as found in U.S. Pat. Nos. 5,180,705 and 5,314,998 such that G1 and G2 may be contained within or pendant from at least one of Z1 and Z2;

R represents a hydrogen atom, a halogen atom, an alkyl group, an acylamino group, an alkoxy group, a sulfonamido group, an aryl group, a thiol group, an alkylthio group, an arylthio group, an alkylamino group, an arylamino group, an amino group, an alkoxycarbonyl group, an acyloxy group, a nitro group, a cyano group, an alkylsulfonyl group, an arylsulfonyl group, an alkylsulfoxyl group, an arylsulfoxyl group, an aryloxyl group, a hydroxyl group, a thioamido group, a carbamoyl group, a sulfamoyl group, a formyl group, an acyl group, a ureido group, an aryloxycarbonyl group, a silyl group, or a sulfoalkoxy group;

L1 represents a nitrogen heterocycle, substituted with R1 or R2 or both R1 and R2;

R1 and R2 each independently represent a hydrogen, a halogen atom (such as iodine, chlorine or bromine) an alkyl group, including vinyl groups, hydroxyalkyl groups, and the like, an acylamino group, an alkoxy group, a sulfonamido group, an aryl group, an alkylthio group, an alkylamino group, an alkoxycarbonyl group, an acyloxy group, an alylsulfonyl group, an alkylsulfoxyl group, an alkylcarbamoyl group, an alkylsulfamoyl group, a formyl group, an acyl group, a silyl group, or a sulfoalkoxyl group;

L2 represents a monodentate or polydentate (e.g., bidentate) ligand;

X represents nitrogen or a methine group;

M is a divalent or polyvalent transition metal ion where the coordination number is at least 4;

and k, m, and n are whole numbers less than or equal to 3, and wherein the method further comprises exposing the combination to light.

Where the term "group" or "nucleus" is used in describing substituents, substitution is anticipated on the substituent. For example, "alkyl group" includes vinyl groups, ether groups (e.g., $CH_3-CH_2-CH_2-O-CH_2-$), haloalkyls, nitroalkyls, carboxyalkyls, hydroxyalkyls, etc. Similarly, the term "arene nucleus" refers, for example, to not only phenyl, but to chlorophenyl, ethylphenyl, and naphthyl as well.

In another embodiment of this invention, the invention relates to metal-containing compounds and to a method for limiting the growth and/or the presence of a virus, a bacterium or fungus by contacting the virus, bacterium or fungus with a metal-containing compound having the following formula:

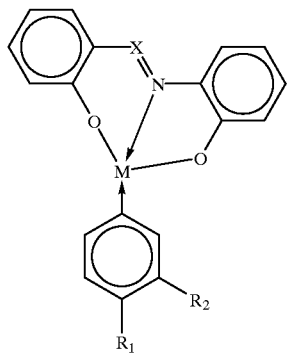

where X is a nitrogen atom or CH group, R1 is a hydrogen atom, a halogen (such as, for example, iodine, chlorine or bromine), a vinyl group, or an alkyl group comprising less than eight carbon atoms; R2 is a hydrogen atom, a halogen (such as, for example, iodine, chlorine or bromine), or an alkyl group comprising less than eight carbon atoms, and M is a platinum atom, a palladium atom, or a nickel atom. Preferably at least one of R1 and R2 is $CH_2OH$ or $CH_2CH_3$. In a preferred embodiment of a metal-containing compound with the above formula R1 is preferably $CH_2OH$ or $CH_2CH_3$, R2 is H, X is methine (CH) group and M is Pt.

The term "alkyl group" also refers not only to unsubstituted alkyl groups such as methyl, ethyl, hexyl, iso-pentyl, cyclohexyl, and the like, but also substituted alkyl groups including, but not limited to, hydroxymethyl, hydroxyethyl, omega-chlorohexyl, and the like, and including perfluoroalkyl such as perfluoromethyl, perfluoroethyl, perfluorohexyl, perfluorocyclohexyl, perfluoroiso-octyl, and the like, but excluding aminomethyl. The method further comprises exposing the metallized compound to light.

Both DNA and RNA viruses (including RNA retroviruses) are inactivated, and gram-negative bacteria, gram-positive bacteria, and fungi are limited in growth, using the compounds of the present invention at a dosage of as little as about 0.001 μg/mL alone or in combination with light and preferably at a dosage of at least about 0.1 μg/mL alone or in combination with light. An "effective amount" of one or more of the compounds of this invention refers to an amount of the compound that is sufficient to limiting the growth and/or the presence of a virus, a bacterium or fungus.

There are a variety of viruses that can be inactivated using the methods of this invention. These viruses include viruses with single or double-stranded nucleic acid genomes, DNA or RNA viruses and including enveloped as well as some non-enveloped viruses. Preferred viruses that are inactivated using the compounds of the present invention are enveloped viruses. A number of viruses representing a variety of structures, sizes and genomes have been tested using the methods of this invention. The examples (below) provide specific exemplary methods for determining whether a particular type of virus, fungus or bacterium is inhibited by the metal-containing compounds of this invention with or without exposure to light. Those of ordinary skill in the art of microbiology will be able to determine whether a particular compound of this invention limits the growth and/or the presence of a virus, a bacterium or fungus according to this invention and in view of the art of microbiology without undue experimentation.

Viruses that comprise negative single-stranded RNA genomes include viruses of the family Orthomyxoviridae, Rhabdoviridae, Paramyxoviridae, Bunyaviridae, and Filoviridae. These are enveloped viruses. Orthomyxoviridae include the influenza viruses A, B, and C. Rhabdoviridae include rabies virus and vesicular stomatitis virus. Paramyxoviridae include parainfluenza virus of mammals (including mumps virus) and pneumovirus (such as respiratory syncytial viruses of man and cattle). Bunyaviridae include hantavirus, which causes Korean hemorrhagic fever and hantavirus pulmonary syndrome. Filoviridae include Marburg virus and Ebola virus.

Viruses that comprise positive single-stranded RNA genomes include Picornaviridae (non-enveloped), Retroviridae, and Togaviridae. Picornaviridae include polioviruses, coxsackieviruses, hepatitis A virus, and rhinovirus. Retroviridae include, for example, human immunodeficiency virus (HIV), simian immunodeficiency virus (SIV), and equine infectious anemia virus (EIAV). Togaviridae include Semliki Forest virus, yellow fever virus, Dengue virus, tick-borne virus, and rubella virus. Parvovirus (non-enveloped) primarily infects cats and dogs.

All other DNA viruses are double-stranded. Double-stranded viruses include Papovaviridae, Adenoviridae, Herpesviridae, Poxviridae, and Hepadnaviridae, With the exception of the Herpesviridae, these viruses are non-enveloped viruses. Papovaviridae include papillomaviruses causing warts and tumors. Adenoviridae include Mastadenovirus and a variety of viruses capable of infecting the respiratory tract. Herpesviridae include herpes simplex 1 and 2, varicella zoster virus, cytomegalovirus, Epstein-Barr virus, human herpesvirus 6, and human herpesvirus 7. Poxviridae include variola, and other pox-inducing virus. Hepadnaviridae include human hepatitis B virus.

A variety of bacteria are growth inhibited by the metal-containing compounds of this invention in combination with light. These include, but are not limited to, *Proteus vulgaris, Enterococcus faecalis, Escherichia coli, Klebsiella pneumoniae, Staphylococcus epidermidis*, and Salmonella sp. Optionally at least some of the metal-containing compounds of this invention can be used to impart antimicrobial activity without light.

Other bacteria that can be tested for growth inhibition in the presence of the metal-containing compounds of this invention include, but are not limited to, Staphylococcus, Streptococcus, Corynebacterium, and Listeria (gram-positive bacteria), Neisseria, Enterobacteriaceae (also called coliforms, includes the genera Escherichia, Salmonella, Shigella), Campylobacter, and Legionella (gram negative bacteria). The coliforms are gram-negative rods (bacilli) that colonize the intestinal tract of humans and other animals. These bacteria are associated with disease. Surfaces and liquids contaminated with these and other bacteria can be exposed to the compounds of this invention to limit their pathogenic potential.

Several pathogenic species of fungi exist, including *Candida albicans* which causes a yeast infection of the oral cavity known as thrush and an infection of the female reproductive tract known as vulvovaginitis. *Candida albicans* is becoming increasingly common as an agent causing infection and pathogenic sequelae. This organism is representative of fungi for purposes of this invention. Those of ordinary skill in the art of microbiology will appreciate that other fungi can be tested for their sensitivity to the compounds of this invention in view of the examples.

The compounds of the present invention can be synthesized from the corresponding o,o'-dihydroxyazo compound dianion as described in the examples by displacement of three chlorines in the required tetrachlorometallate and subsequent loss of the remaining chlorine coincident with substitution of a nitrogen heterocycle. Methods for synthesizing the metal-containing compounds of this invention are described in U.S. Pat. Nos. 5,180,705 and 5,314,998.

The synthesized compounds can be used in liquid or powder form. In one embodiment, the metal-containing compounds of this invention are used as a liquid and can be dissolved in a suitable solvent such as dimethyl sulfoxide. Other solvents that can be used include N,N-dimethylformamide, ethanol, oils such as cottonseed oil, methanol, chloroform, dichloromethane, and the like, as well as solvent mixtures containing water and dimethyl sulfoxide, ethanol, methanol, or N,N-dimethylformamide. The dissolved compound, or a mixture of compounds according to this invention, or one or more compounds of this invention alone or in combination with one or more virucidal, bactericidal or static, and/or fungicidal or static agents (such as a polymixin, another antibiotic, a virucide, and/or a fungicide) is applied to a surface or used as a solid or liquid and applied to a solid or liquid to limit growth or prevent viral or bacterial or fungal contamination. Alternatively, one or more compounds of this invention alone or in combination with one or more virucidal, bactericidal or static and/or fungicidal or static agents can be added directly to a solid or liquid that is virus-laden or bacteria-laden or contaminated with fungus.

The compounds of the present invention are extremely light and heat stable. Solutions of the metal-containing compounds can be prepared in DMSO at an optical absorption of approximately 1.0 at the wavelength of maximal absorption of the metal-containing compound between about 400 nm to about 700 nm. Solutions prepared in this way do not show substantial changes in absorption spectrum (including optical density) after six months storing in room light. The metal-containing compounds are also stable at temperatures up to at least 200° C.

In one aspect of this invention, the compounds of this invention can be exposed to light to promote the ability of the compounds to inhibit microbial growth. Some of the compounds of this invention are active independent of the presence of light while others are active in the presence of light.

The light exposure can include exposure from a directed light source or from ambient light. Preferably the compounds of this invention are exposed to light of wavelengths of at least about 200 nanometer (nm) and less than about 900 nm. More preferably the light has a wavelength of at least about 400 nm and less than about 850 nm. Convenient and sufficient light sources are those typically used for fluorescent lighting of laboratories and offices as well as Light Emitting Diode (LED) sources, incandescent sources, sunlight and lasers. The individual compounds of this invention can optimally be activated with a particular wavelength of light. Without intending to limit the scope of this invention, the spectral output of the light source likely overlaps with the absorption spectrum of the metal-containing compound as measured in the solvent used for administering the compound. In one embodiment, the compounds are activated by exposing the compounds to an irradiance of at least about 270 $\mu W/cm^2$ for about five minutes, but those of ordinary skill in the art will readily appreciate that brighter light sources allow for reductions in the duration of illumination time.

Light activation can occur with continuous, pulsating or periodic exposure to light. Those of ordinary skill in the art will recognize that optimal activation will depend on the intensity and the duration of light but that a range of intensities and durations of light exposure can be used to activate the light-responsive compounds of this invention.

The concentration of the compound and the light source, intensity or irradiance, spectral properties of the light source, and duration of the illumination can affect the performance of the light-responsive compounds. Those of ordinary skill in the art will appreciate that concentration, light intensity, and the like can be optimized in view of this specification without undue experimentation. Methods are provided in the examples for preferred techniques and formats for optimizing the growth-inhibiting properties of these compounds. Other testing regimes can be readily generated by those skilled in the art, particularly in view of the guidance provided throughout the examples and in view of clinical laboratory testing standards and manuals. Preferred concentrations of the compounds will vary depending on use. A preferred concentration range for the compounds is from about 0.01 $\mu g/mL$ to about 10 mg/mL; however, many of the compounds will be active at lower concentrations.

In another aspect of this invention, the compound or a mixture of compounds according to this invention, or one or more compounds of this invention can be combined with one or more virucidal, bactericidal, or fungicidal agents (such as a polymixin or another antibiotic).

The compounds of this invention, alone or in combination with other antimicrobial compounds can be applied, coated, sprayed, dried onto, used as a dip, impregnated into or compounded with, onto a solid or porous surface or added to a liquid. The compounds of this invention can be applied to solid surfaces to limit the growth of microbial agents. The compounds can be applied to woven or nonwoven fabrics, or combined with a variety of solids such as inorganic materials such as hydroxyapatite, silica, or glass to inhibit, limit, reduce and/or prevent virus, bacterial, or fungal contamination. The compounds of this invention can be applied to disposable surfaces such as paper, tissues, cotton swabs, surgical wear, drapes as well as applied to a variety of absorbent and nonabsorbent materials.

The incorporation of the compounds of this invention into fabrics or porous polymers advantageously can prevent degradation of the fibers or material. The incorporation of the compounds of this invention into fabrics or porous polymers also can result in killing of infiltrated or sequestered bacteria and fungi within the fibers or material, as in air or water filters, for example.

The compounds of this invention can be incorporated into cloth for use as antimicrobial wipes. Similarly, the compounds can be used for surface sterilization, for example, in home, day-care, industrial, and hospital settings, for cleansing toys, equipment, medical devices and work surfaces. A variety of equipment, disposables and devices such as sutures and bandages, hypodermic needles and containers can be sterilized using the compounds, according to this invention.

The preparation of the metal-containing compounds and the performance of the compounds of this invention in inactivating viruses, inhibiting viral replication and in limiting the growth or presence of bacteria and fungi are demonstrated in the following examples. All references and publications are incorporated by reference into this disclosure.

EXAMPLE 1

Synthesis of the Metal-Containing Compounds

Reagents for chemical synthesis were obtained from Aldrich (Milwaukee, Wis.) unless otherwise noted. Compounds 1A–1I, 1L, and 3 thru 19 were synthesized according to the procedures disclosed in U.S. Pat. Nos. 5,180,705 and 5,314,998. Compound 20 was purchased from Aldrich, Milwaukee, Wis., and compound 21 is available from TCI-America, Portland, Oreg.

Synthesis of Compound 1J

A solution of 2-salicylideneaminophenol (0.320 g, 1.5 mmol, TCI-America, Portland, Oreg.) in dimethyl sulfoxide (15 mL) at 100° C. was added to a solution of potassium tetraclhloroplatinate (0.685 g, 1.65 mmol) in dimethyl sulfoxide (15 mL) at 100° C. Next, potassium carbonate (0.600 g) was added and the resulting mixture heated at 150° C. for 10 min. The reaction mixture was allowed to cool to 100° C. and then 4-vinylpyridine (0.600 mL) was added. The reaction mixture was stirred at room temperature for 18 h. The reaction mixture was poured into water (50 mL) and then extracted once with diethyl ether (150 mL) and once with chloroform (150 mL). The diethyl ether and chloroform extracts were combined. The combined extracts were washed sequentially with 3N hydrochloric acid (twice 50 mL), water (twice, 100 mL), and once with a saturated aqueous NaCl solution.

The organic solution was dried over anhydrous magnesium sulfate, filtered and concentrated to give an orange solid. The solid was dissolved in a minimum amount of chloroform and passed through a column of silica gel (20×5 cm) while eluting the column with chloroform (250 mL). The eluent was again concentrated to give an orange solid. The solid was recrystallized from ethanol to give 0.068 g of compound 1J as an orange solid; $^1$H NMR (500 MHz; CDCl$_3$): δ 5.70 (d, 1H, J=10.8 Hz); 6.14 (d, 1H, J=17.6 Hz); 6.70–6.82 (m, 3H); 7.10–7.17 (m, 2H); 7.26–7.28 (m, 1H); 7.46–7.51 (m, 3H); 7.66 (dd, 1H, J1=7.9 Hz, J2=1.6 Hz); 7.81 (d, 1H, J=8.3 Hz); 8.65 (s, 1H); 9.16 (dd, 1H, J1=5.4 Hz, J2=1.6 Hz); $^{13}$C{$^1$H} NMR (125 MHz; CDCl$_3$): δ 114.21, 115.23, 116.08, 117.77, 121.14, 121.56, 121.67, 128.16, 132.34, 133.04, 133.25, 140.00, 142.77, 146.45, 149.26, 161.75, 167.01.

Synthesis of Compound 1K

A solution of 2-salicylideneaminophenol (0.320 g, 1.5 mmol, TCI-America, Portland, Oreg.) in dimethyl sulfoxide (15 mL) at 100° C. was added to a solution of potassium tetrachloroplatinate (0.685 g, 1.65 mmol) in dimethylsulfoxide (15 mL) at 100° C. Next, potassium carbonate (0.600 g) was added and the resulting mixture heated at 150° C. for 10 min. The reaction mixture was allowed to cool to 100° C. and then 4-pyridinecarbinol (0.607 g) was added. The reaction mixture was stirred at room temperature for 18 h. The reaction mixture was poured into water (50 mL) and then extracted once with diethyl ether (150 mL) and once with chloroform (150 mL). The diethyl ether and chloroform extracts were combined. The combined extracts were washed sequentially with 3N hydrochloric acid (twice 50 mL), water (twice 100 mL), and once with a saturated aqueous solution of NaCl. The organic solution was dried over anhydrous magnesium sulfate, filtered and concentrated to give an orange solid. The solid was recrystallized from ethanol to give 0.080 g of 1K as dark brown crystals; $^1$H NMR (500 MHz; d6-DMSO): δ 4.70 (d, 2H, J=5.6 Hz); 5.67 (t, 1H, J=5.6 Hz); 6.67 (dt, 1H, J1=7.3 Hz, J2=1.6 Hz); 6.78 (t, 1H, J=7.3 Hz); 7.00–7.08 (m, 2H); 7.21 (d, 1H, J=8.3 Hz); 7.47 (dt, 1H, J1=7.7 Hz, J2=1.7 Hz); 7.66 (d, 2H, J=6.6 Hz); 7.88 (dd, 1H, J1=8.1 Hz, J2=1.7 Hz); 8.09 (d, 1H, J=8.4 Hz).

Synthesis of Compound 2

A. Synthesis of Ligand:

A solution of 2-aminophenol (0.545 g, 5.0 mmol), water (5 mL) and concentrated hydrochloric acid (1.25 mL) was heated at reflux for 1.5 h. The solution was cooled to 5° C. and then a solution of sodium nitrite (0.348 g, 5.05 mmol) in water (3 mL) was added. After 20 min. the resulting solution was added to a solution of dimedone (0.700 g, 5.0 mmol) in water (10 mL) and pyridine (10 mL) at 5° C. The resulting mixture was maintained at room temperature for 18 h. The reaction mixture was filtered and the residue washed with a small quantity of water. The solid was recrystallized from ethanol to give 0.597 g (46% yield) of the precursor compound as an orange crystalline solid; m.p. 221–223° C.; $^1$H NMR (500 MHz; CDCl$_3$): δ 1.14 (s, 6H); 2.59 (s, 2H); 2.62 (s, 2H); 6.91 (dt, 1H, J1=7.5 Hz, J2=1.5 Hz); 7.04–7.11 (m, 2H); 7.14 (dt, 1H, J1=7.2 Hz, J2=1.5 Hz); 10.29 (bs, 1H); 15.41 (bs, 1H); $^{13}$C{$^1$H} NMR (125 MHz; CDCl$_3$): δ 28.47, 30.98, 51.81, 52.15, 118.99, 119.02, 119.99, 125.47, 127.16, 128.21, 149.72, 191.71, 196.98; IR(KBr): 3180, 1650, 1616, 1593, 1466, 1389, 1326, 1299, 1222, 759 cm-1; HRMS: (cal) 260.1155, (exp) 260.1159

B. Synthesis of Metal Complex:

A solution of the precursor compound (0.390 g, 1.5 mmol) in dimethylsulfoxide (15 mL) at 100° C. was added to a solution of potassium tetrachloroplatinate (0.685 g, 1.65 mmol) in dimethylsulfoxide (15 mL) at 100° C. Next, potassium carbonate (0.600 g) was added and the resulting mixture heated at 150° C. for 10 min. The reaction mixture was allowed to cool to 100° C. and then freshly distilled 4-vinylpyridine (0.600 mL) was added. The reaction mixture was stirred at room temperature for 18 h. The reaction mixture was poured into water (50 mL). The mixture was cooled in an ice bath and then filtered. The residue was dissolved in dichloromethane (25 mL). The solution was dried over anhydrous magnesium sulfate, filtered and concentrated to give a dark orange solid. The solid was recrystallized from ethanol to give 0.407 g (49.0% yield) of compound 2 as dark orange crystalline solid; $^1$H NMR (400 MHz; CDCl$_3$): δ 1.13 (s, 6H); 2.42 (s, 2H); 2.60 (s, 2H); 5.74 (d, 1H, J=10.6 Hz); 6.17 (d, 1H, J=17.6 Hz); 6.70–6.80 (m, 2H); 7.14–7.20 (m, 2H); 7.51 (d, 2H, J=6.6 Hz), 8.27 (dd, 1H, J1=8.3 Hz, J2=1.3 Hz); 8.96 (d, 2H, J=6.2 Hz); $^{13}$C{$^1$H} NMR (125 Mz; CDCl$_3$): δ 28.20, 30.36, 48.58, 51.85, 116.54, 117.05, 117.81, 122.09, 122.24, 130.34, 133.21, 133.94, 146.80, 147.70, 149.39, 167.20, 167.55, 194.64; IR(KBr): 1662, 1620, 1592, 1476, 1440, 1418, 1382, 1312, 1274, 1107, 749, 511 cm$^{-1}$; HRMS: (cal) 558.1225, (exp) 558.1222.

Compound 1

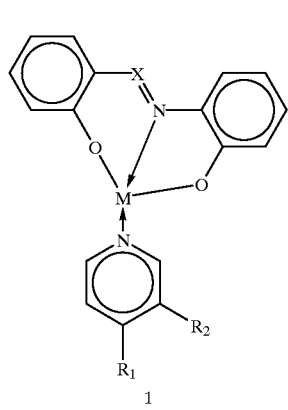

Compound 2

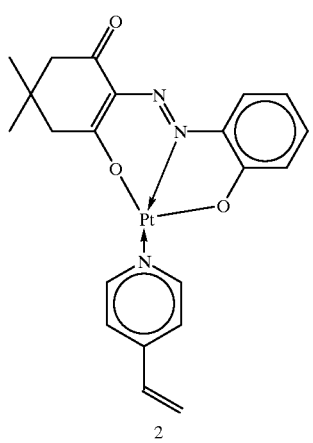

Compound 3

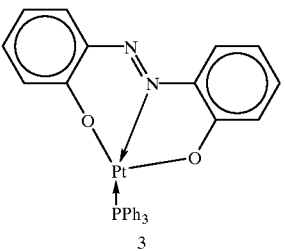

Compound 4

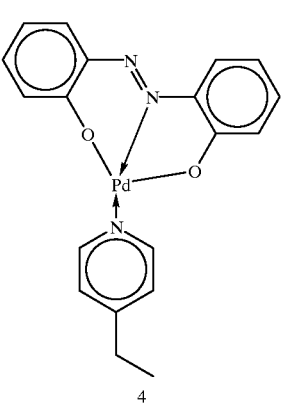

Compound 5

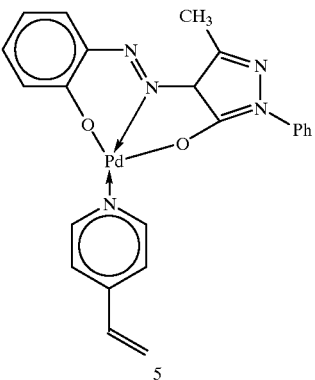

Compound 6

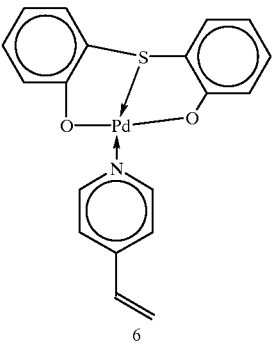

-continued
Compound 7
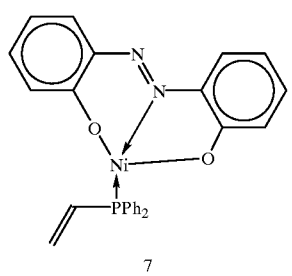
7
Compound 8
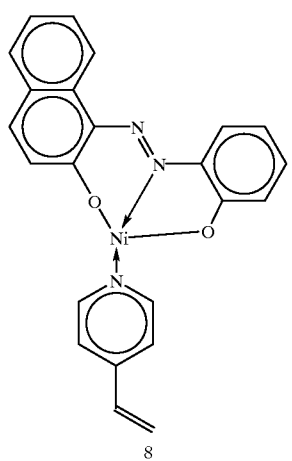
8
Compound 9
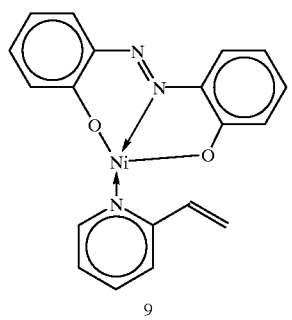
9
Compound 10
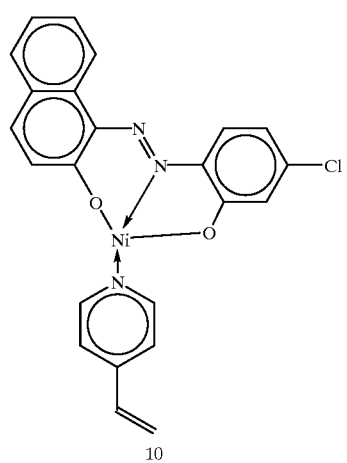
10
Compound 11
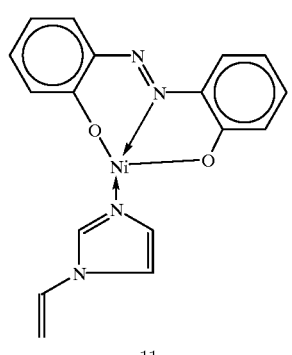
11
Compound 12
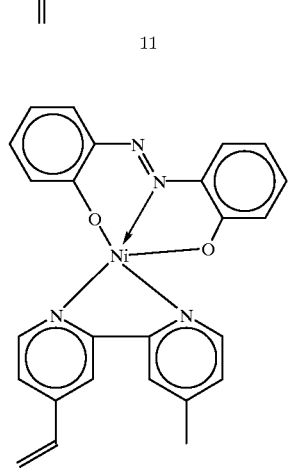
12
Compound 13
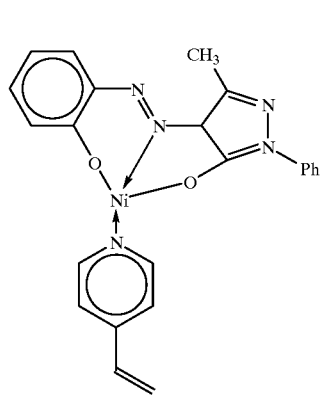
13
Compound 14
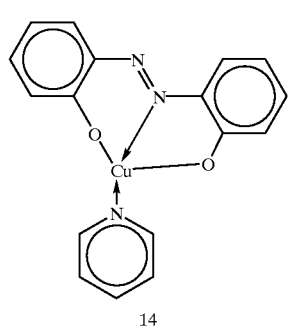
14

Compound 15

15

Compound 16

16

Compound 17

17

Compound 18

18

Compound 19

19

Compound 20

20

Compound 21

21

Compound 22

22

EXAMPLE 2

Testing of Metal-Containing Compounds for
Virucidal Activity Against Equine Infectious
Anemia Virus (EIAV)

The aforementioned compounds (Compounds 1A–1L and 2–21) were tested for virucidal activity using, EIAV. Reduction in EIAV infectivity was tested using equine dermal (ED) cells (ATCC CCL57, American Type Culture Collection, Rockville, Md.). The procedure used was as follows:

ED cells were seeded onto 6-well tissue culture plates (Corning Co., #25810) at $5 \times 10^5$ cells per well in Dulbecco's Modified Eagle's Medium (#D5648) with 20% fetal calf serum (GibcoBRL Co., #26140-038). The cells were incubated (under 5–10% $CO_2$ in air) for about 24 hours at 37° C.

Virus was treated with the metal-containing compound as follows: Unless otherwise noted, all experimental manipulations were done in ambient light. A test solution was prepared using 10 microliters ($\mu$l) of stock solutions of metal-containing compound in dimethyl sulfoxide (1 mg/mL). This was added to $10^4$ infectious units of EIAV in 1.0 mL Hanks balanced buffer solution without calcium chloride or magnesium sulfate (HBSS, Sigma Chemical Co., #H2387) with 2% fetal calf serum. Samples were placed in individual wells of duplicate 24-well tissue culture plates (Corning, #25820). One plate was wrapped in aluminum foil and served as the dark control. The other plate was placed on a benchtop and exposed to fluorescent room light (irradiance=272 $\mu$W/cm$^2$) for 30 minutes (except where noted below) at room temperature.

ED cells in the 6-well plates were inoculated with polybrene (Sigma Chemical Co., #P4515) to a final concentration of 8 $\mu$l/mL and with either 10 $\mu$l or 100 $\mu$l of test solution (supra) containing the metal-containing compound. Cells were incubated 5 days at 37° C. in the dark. Samples were tested on the seventh day of the experiment for the presence of virus using the focus forming assay provided below:

Medium was aspirated from the wells and cells were rinsed once with 3 mL TNF (10 mM Tris (pH 7.5), 150 mM NaCl, 1% fetal bovine serum) and fixed with 100% methanol for 5 min. Cells were rinsed twice with 3 mL TNF and incubated 30 min with 0.5 mL horse anti-EIAV serum (convalescent sera at 1:800 dilution in HBSS) with rocking. Cells were rinsed three times with 3 mL TNF and incubated for 30 min with 0.5 mL anti-horse HRP antibody (Cappel/Organon Teknika Corp., Lot #35426) with rocking. Following this step, cells were rinsed three times with 3 ml TN (no FBS) and incubated with 2 mL AEC substrate (Sigma Chemical Co., #A6926) in 0.05 M sodium acetate/N,N-dimethyl formamide (Sigma Chemical Co., #D8654) buffer for 20 min in the dark. Cells were rinsed with distilled water and allowed to dry. Positive foci of infected cells were counted using microscopy and the number of focus forming units (FFU) per mL of inoculum was calculated. The FFU of samples treated with the potential virucidal agent and light was compared to those for samples kept in the dark. Dark controls were run only for those experiments in which significant reduction in virus titer was first noted at a level of greater than about 75% as compared to controls when tested at a compound concentration of 10 μg/mL (with the exception of compounds 1L, 2, 20, and 21).

In another set of experiments, a 5 mL sample of phiX174 bacteriophage at $10^9$ pfu(plaque forming units)/ml was filtered through a 50 mm diameter pre-filter (Nalgene catalog #281-5000, Nalge Products, Rochester, N.Y.) coated with metal-containing compound 1L. No reduction in infectivity of the virus for *E. coli* was observed.

TABLE 1

Virucidal Activity Of Compounds 1A-1L (in FFU/mL)

| Compound | Substitutions | 10 μg/mL (light) | 1.0 μg/mL (light) | 0.1 μg/mL (light) | 10.0 μg/mL (dark) |
|---|---|---|---|---|---|
| 1A | R1 = vinyl, R2 = H, X = N, M = Pt | 0 | 0 | 1412 | 5248 |
| 1B | R1 = $CH_2OH$, R2 = H, X = N, M = Pt | 0 | 0 | 2398 | 5623 |
| 1C | R1 = $CH_2NH_2$, R2 = H, X = N, M = Pt | 10,964 | | 15,135 | |
| 1D | R1 = $C_8H_{17}$, R2 = H, X = N, M = Pt | 41,686 | | 100,0000 | |
| 1E | R1 = 5-nonyl, R2 = H, X = N, M = Pt | 15,848 | | 47,863 | |
| 1F | R1 = $C_2H_5$, R2 = H, X = N, M = Pt | 0 | 302 | 3715 | 7079 |
| 1G | R1 = CHO, R2 = H, X = N, M = Pt | 302 | 5495 | 5012 | 8709 |
| 1H | R1 = H, R2 = H, X = N, M = Pt | 0 | 0 | 8511 | 7244 |
| 1I | R1 = H, R2 = $CH_2OH$, X = N, M = Pt | 0 | 0 | 26,915 | 53,703 |
| 1J | R1 = vinyl, R2 = H, X = CH, M = Pt | 0 | 0 | | 25,703 |
| 1K | R1 = $CH_2OH$, R2 = H, X = CH, M = Pt | 0 | 0 | 25,118 | 83,176 |
| 1L | R1 = vinyl, R2 = H, X = N, M = Pd | 0 | | 12,022 | |

TABLE II

Virucidal Activity of Compounds 2–21 (in FFU/mL)

| Metallized Compound | 10 μg/mL (light) | 1.0 μg/mL (light) | 0.1 μg/mL (light) | 10 μg/mL (dark) |
|---|---|---|---|---|
| 2 | 10,964 | 8,912 | | 15,848 |
| 3 | 31,622 | | 100,000 | |
| 4 | 12,882 | | 19,952 | |
| 5 | 15,135 | | 25,118 | |
| 6 | 19,054 | | 25,118 | |
| 7 | ** | | 53,703 | |
| 8 | 25,703 | | 25,118 | |
| 9 | 26,915 | | 23,988 | |
| 10 | 19,054 | | 23,988 | |
| 11 | 21,877 | | 28,183 | |
| 12 | 14,125 | | 23,988 | |
| 13 | 25,118 | | 21,877 | |
| 14 | 16,982 | | 16,982 | |
| 15 | 19,054 | | 19,952 | |
| 16 | 14,125 | | 19,054 | |
| 17 | 22,908 | | 22,908 | |
| 18 | 15,135 | | 15,135 | |
| 19 | 5,888 | | 7,079 | |
| 20 | 5,011 | 10,964 | 10,964 | 6760 |
| 21 | 12022 | 16,982 | 10,964 | 7,943 |

** indicates sample toxic to ED cells at that dose

The results indicated that compounds 1A, 1B, and 1F–1L reduced of infectious EIAV particles by at least 75% in equine dermal cells. Compounds 20 and 21 were not effective in this study. It is surprising that the compounds of the present invention, while incorporating the compounds 20 and 21, showed antimicrobial activity when combined with metal and N-heterocycle moieties.

The compounds were also tested for the effect of length of light exposure time on virucidal activity. For example, when a 10 µg/mL solution of compound 1A was exposed to light for 5 min there was a reduction in the viral titer. Increasing light exposure to 15 min further reduced the viral titer. These experiments indicate that shorter irradiation times can lead to reduction in viral titer but that longer exposures to light can further enhance the virucidal effect of the compounds.

EXAMPLE 3

Testing of Compounds for Virucidal Activity Against Human Immunodeficiency Virus 1 (HIV-1) and Herpes Simplex Virus-1 (HSV-1)

0.1 mL concentrated HIV/RF (prepared by ultracentrifuge and resuspended in 5% RPMI 60/40 media with 5% Fetal Bovine Serum, NIAID, Bethesda, Md.) was added to 0.9 mL of compounds 1A, 1B, 1H and 1K in DMSO solution in a 24-well plate. The plate was allowed to sit under regular fluorescent lighting on the lab benchtop for 30 min. Next, 10-fold serial dilutions were prepared of the compounds and these were used to inoculate MT2 cells (NIAID Cat #237) at $10^4$ cells/well. Plates were allowed to incubate at 37° C., 5% $CO_2$ in air for seven days. Virus was counted by observing foci of virus cytopathology. The results are indicated below as Log Reduction in Virus Titer.

The compounds were also tested for their activity against HSV. The protocol was essentially identical to that for HIV-1 testing, except that Vero cells (American Type Culture Collection, Rockville, Md., #CCL81) were inoculated with HSV-1 incubated with compound 1A and virus was quantitate by plaque assay.

TABLE III

| | | Log Reduction in Virus Titer | | | |
|---|---|---|---|---|---|
| | | | light | | dark |
| Compound | Virus Tested | 10 µg/mL | 1.0 µg/mL | 0.1 µg/mL | 10.0 µg/mL |
| 1A | HIV-1 | >4.0 | 0 | 0 | |
| 1B | HIV-1 | >4.5 | 4.0 | 0 | |
| 1H | HIV-1 | >4.5 | 0.8 | 0 | |
| 1K | HIV-1 | >4.5 | 0.8 | 0 | |
| 1A | HSV-1 | 3.7 | 1.7 | 0.3 | 0.3 |

The results indicated that the compounds of the present invention were effective in inactivating the RNA retrovirus HIV-1 and the DNA virus HSV-1.

EXAMPLE 4

Testing of Compounds for Prevention of Growth of Bacteria

The aforementioned compounds were tested as solutions of compound in dimethyl sulfoxide at several concentrations for prevention of growth of gram-positive and gram-negative bacteria. The procedure used was as follows:

Bacteria that had been grown at 37° C. overnight in Todd Hewitt broth (purchased from DIFCO, Detroit, Mich.) were diluted with Todd Hewitt broth to a concentration of approximately $1\times10^8$ colony forming units (CFU)/mL, as measured by light scattering at 600 nm using VIS spectroscopy. Subsequently, 1.0 mL of the bacteria-laden broth was transferred to a petri plate containing brain heart infusion agar (purchased from DiMed Corp., St. Paul, Minn.), spread evenly on the ajar surface and allowed to dry for thirty minutes at room temperature. Seven millimeter (mm) diameter paper filter disks were placed on the agar plates on top of the bacteria. Each disk was treated with either 5.0 µL of dimethyl sulfoxide as a negative control, 0.12% aqueous chlorhexidine gluconate solution (positive control), or the compounds of this invention as solution in dimethyl sulfoxide, using at least three different concentrations of each compound tested. The plates were either kept in the dark (control) or exposed to light either before or during incubation at 37° C. for 24 hr. (as described specifically for each experiment below). In all cases, anaerobic bacteria and facultative anaerobes were placed in air tight containers that were under anaerobic atmosphere (4–10% $CO_2$ in air; $O_2$ removed by combination with $H_2$ to form $H_2O$, Gas Pak Plus, Benton Dickinson, Cockeysville, Md.)

Following a twenty-four hour incubation, the plates were removed from the incubator and inspected for areas of clearing surrounding the 7 mm filter disks. The diameter of each clear area was measured, recorded and compared with controls.

Testing of Compound 1H for Growth Inhibition of Bacteria Using 30 Minute Light Exposure In this experiment, one half of the plates were placed on the laboratory bench in the light for 30 minutes at room temperature immediately before incubating for 24 hours in the dark; the other half of the samples were placed into the dark incubator for 24 hours without light exposure. Monolayers of Streplococcus gordonii, Streptococcus sobrinus, Streptococcus mutans, Actinomyces viscosus, and Actinomyces naeslundii were exposed to compound 1H in DMSO, DMSO alone or a positive control (chlorhexidrine gluconate).

The term "% dia (dark)" indicates percentage of diameter of zone of growth inhibition for compound kept in the dark as compared with zone of growth inhibition for chlorhexidine gluconate control kept in the dark.

The term "% dia (light)" indicates percentage of diameter of zone of growth inhibition for compound exposed to ambient light for 30 min prior to incubation in the dark as compared with zone of inhibition for chlorhexidine gluconate control treated in the same manner.

TABLE IV

Growth Inhibition of Bacteria in Presence of Compound 1H.

| Bacterium | Conc. Of compound tested (µg/mL) | % dia (light) | % dia (dark) |
|---|---|---|---|
| S. gordonii | 0.32 | 0 | 0 |
| | 3.2 | 53 | 0 |
| | 32 | 53 | 0 |
| S. sobrinus | 0.32 | 0 | 0 |
| | 3.2 | 40 | 0 |
| | 32 | 45 | 0 |

TABLE IV-continued

Growth Inhibition of Bacteria in Presence of Compound 1H.

| Bacterium | Conc. Of compound tested (µg/mL) | % dia (light) | % dia (dark) |
|---|---|---|---|
| S. mutans | 0.32 | 43 | 0 |
| | 3.2 | 49 | 0 |
| | 32 | 51 | 0 |
| A. viscosus | 0.32 | 29 | 0 |
| | 3.2 | 35 | 0 |
| | 32 | 38 | 31 |
| A. naeslundii | 0.32 | 37 | 0 |
| | 3.2 | 39 | 31 |
| | 32 | 41 | 22 |

The results indicated that 1H inhibited bacterial growth at the concentrations of compound in DMSO tested when the compound was exposed to light for 30 minutes prior to incubation in the dark. Additionally, 1H inhibited growth of Actinomyces in DMSO both when placed in the light prior to incubation in the dark, and also when kept in the dark. DMSO-only treated cultures demonstrated no growth inhibition.

EXAMPLE 5

Growth Inhibition of Bacteria using Continuous Light Exposure.

Compound 22 (structure provided supra) was prepared according to the procedures disclosed in U.S. Pat. Nos. 5,180,705 and 5,314,998. The remaining compounds were prepared as described previously.

In these experiments, bacterial lawns were exposed to 7 mm diameter paper filter disks moistened with the designated compound. All plates were placed 16 inches below a lamp (Sylvania F15Y8-W fluorescent bulb) inside an incubator and irradiated continuously during the experiment (24 hours). Growth inhibition was tested at 100 µg/mL and 0.1 µg/mL of compound in DMSO. A 0.12% aqueous chlorhexidine gluconate control experiment and a neat DMSO control were included. Bacteria tested included *Proteus vulgaris, Enterococcus faecalis, Escheria coli, Klebsiella pneumonia, Staphylococcus epidermidis,* and Salmonella sp. The term "% dia (light)" indicates percentage of diameter of zone of inhibition of growth for compound tested compared with zone of inhibition for chlorhexidine gluconate control treated in the same manner. In Table V, "*" refers to data points not tested in this study.

TABLE V

Bacteria Growth Inhibition of Compounds 1G, 1H, 1L, 8 and 22.

| Bacterium | Compound | Compound Conc. (µg/mL) | % dia (light) |
|---|---|---|---|
| P. vulgaris | 1G | 0.1 | * |
| | 1G | 100 | * |
| | 1H | 0.1 | 0 |
| | 1H | 100 | 0 |
| | 1L | 0.1 | 0 |
| | 1L | 100 | 0 |
| | 8 | 0.1 | 0 |
| | 8 | 100 | 0 |
| | 22 | 0.1 | 0 |
| | 22 | 100 | 0 |
| E. faecalis | 1G | 0.1 | 0 |
| | 1G | 100 | * |
| | 1H | 0.1 | 0 |
| | 1H | 100 | 65 |
| | 1L | 0.1 | 0 |
| | 1L | 100 | 0 |
| | 8 | 0.1 | 0 |
| | 8 | 100 | <10 |
| | 22 | 0.1 | 0 |
| | 22 | 100 | 0 |
| E. coli | 1G | 0.1 | 0 |
| | 1G | 100 | 0 |
| | 1H | 0.1 | 0 |
| | 1H | 100 | 0 |
| | 1L | 0.1 | 0 |
| | 1L | 100 | 54 |
| | 8 | 0.1 | * |
| | 8 | 100 | 63 |
| | 22 | 0.1 | 0 |
| | 22 | 100 | 0 |
| K. pneumoniae | 1G | 0.1 | 59 |
| | 1G | 100 | 59 |
| | 1H | 0.1 | 52 |
| | 1H | 100 | 52 |
| | 1L | 0.1 | 56 |
| | 1L | 100 | 56 |
| | 8 | 0.1 | 59 |
| | 8 | 100 | 59 |
| | 22 | 0.1 | 62 |
| | 22 | 100 | 58 |
| S. epidermidis | 1G | 0.1 | <10 |
| | 1G | 100 | 64 |
| | 1H | 0.1 | * |
| | 1H | 100 | 53 |
| | 1L | 0.1 | 0 |
| | 1L | 100 | 0 |
| | 8 | 0.1 | 0 |
| | 8 | 100 | 56 |
| | 22 | 0.1 | 0 |
| | 22 | 100 | 0 |
| Salmonella sp. | 1G | 0.1 | 0 |
| | 1G | 100 | 0 |
| | 1H | 0.1 | 0 |
| | 1H | 100 | 0 |
| | 1L | 0.1 | 0 |
| | 1L | 100 | 0 |
| | 8 | 0.1 | 0 |
| | 8 | 100 | 0 |
| | 22 | 0.1 | 0 |
| | 22 | 100 | 0 |

The results indicated that 1G inhibited growth of *S. epidermidis* bacteria at both concentrations tested, 1H inhibited growth of *E. faecalis* at the higher concentration tested, 1L inhibited growth of *E. coli* at the higher concentration tested, compound 8 prevented growth of *E. faecalis, E. coli,* and *S. epidermidis* at the higher concentration tested, and that compound 22 did not inhibit growth of any of the bacteria tested. The DMSO control showed growth inhibition (<10% inhibition for *P. vulgaris* and for *K. pneumoniae*; thus, the data for *K. pneumoniae* do not represent inhibition of growth due to the compounds of this invention).

In another set of experiments (summarized in Table VI), all plates were placed 16 inches below a lamp (Sylvania F15T8-W fluorescent bulb) inside an incubator and irradiated continuously during the experiment (24 hours). No dark control experiment was conducted. The compounds were tested at 10 mg/mL and 0.1 mg/mL compound in DMSO. A 0.12% aqueous chlorhexidine gluconate control experiment was conducted as was a neat DMSO control. Bacterial inhibition was tested for compounds 1F, 1H and 8 for *Streplococcris mutans, Enterococcus faecalis, Escherichia coli*, and Salmonella sp.

The term "% dia (light)" indicates percentage of diameter of zone of inhibition of growth for metal-containing compound tested compared with zone of inhibition for chlorhexidine gluconate control treated in the same manner.

TABLE VI

Bacterial Growth Inhibition Using Compounds 1F, 1H and 8.

| Bacterium | Compound tested | Conc. of compound tested (mg/mL) | % dia (light) |
|---|---|---|---|
| S. mutans | 1F | 0.1 | 70 |
| | 1F | 10.0 | 81 |
| | 1H | 0.1 | 74 |
| | 1H | 10.0 | 66 |
| | 8 | 0.1 | 56 |
| | 8 | 10.0 | 85 |
| E. faecalis | 1F | 0.1 | 80 |
| | 1F | 10.0 | 71 |
| | 1H | 0.1 | 73 |
| | 1H | 10.0 | 69 |
| | 8 | 0.1 | 65 |
| | 8 | 10.0 | 85 |
| E. Coli | 1F | 0.1 | 0 |
| | 1F | 10.0 | 62 |
| | 1H | 0.1 | 54 |
| | 1H | 10.0 | 57 |
| | 8 | 0.1 | 54 |
| | 8 | 10.0 | 54 |
| Salmonella sp. | 1F | 0.1 | 0 |
| | 1F | 10.0 | 82 |
| | 1H | 0.1 | 0 |
| | 1H | 10.0 | 73 |
| | 8 | 0.1 | 0 |
| | 8 | 10.0 | 84 |

The results demonstrated effective inhibition of bacterial growth for two gram-positive and two gram-negative bacteria using all three compounds tested at a concentration of 10.0 mg/mL. Furthermore, prevention of growth of the two gram-positive bacteria occured for all the compounds at a concentration of 0.1 mg/mL and *E. coli* was inhibited by compounds 1H and 8 at 0.1 mg/ml. Importantly, these compounds were able to kill gram-negative bacteria through a light responsive mechanism.

EXAMPLE 6

Demonstration of Inhibition of Bacterial Growth using High Intensity Light

*E. coli* was plated on trypicase soy agar in two petri dishes. One 6 mm paper disk saturated with 10 mg/mL compound 1B in DMSO was placed on the *E. coli* lawn. Additionally a disk with DMSO only was added to each plate. One plate was kept in the dark overnight at room temperature, while the other plate was irradiated continuously with bright light 38 mW/cm$^2$ through two pyrex dishes, one containing 0.5 inches of water, at room temperature overnight.

No zone of inhibition was obsessed for either the DMSO only disk or for the disk containing compound 1B on plates incubated in the dark. A 19 mm zone of inhibition was present surrounding the disk with compound 1B incubated in the light (versus no zone of inhibition for DMSO only disk incubated in the light) demonstrating inhibition of gram-negative bacteria using continuous high-intensity light.

EXAMPLE 7

Testing of Metal-containing Compounds for Bactericidal Activity on a Surface

For this experiment, three hydroxyapatite disks for each compound were moistened with a solution of either 10.0 mg/mL 1L or 10.0 mg/mL 1F in dichloromethane. The six disks, as well as six control disks (no compound), were each placed into wells containing *E. faecalis* bacteria in binding buffer (2 mM $K_3PO_4$, 50 mM KCl, 1 mM $CaCl_2$, pH 6.8) at a concentration corresponding to an optical density of 1.0 at 600 nm. The disks were agitated gently in an incubator at 37° C. for 24 hours with constant light exposure from a desk lamp. The disks were then rinsed with binding buffer and placed in Todd Hewett broth to allow for potential growth of bacteria. The broths were incubated overnight in an incubator, after which 0.1 mL sample from each broth was placed on BHI agar plates, separately, and then the plates were placed in the same incubator overnight.

Results of Testing Compounds 1L and 1F for Prevention of Growth of Bacteria on a Surface The two control disk sets as well as the disk moistened with compound 1F allowed growth of bacteria at the "too numerous to count level". Disks moistened with compound 1L, showed no evidence of bacterial growth on the disk or in the broth indicating that 1L was bactericidal to *E. faecalis*.

EXAMPLE 8

Testing of Metal-Containing Compounds for Growth Inhibition of Fungus

For this experiment, TSA (trypticase soy agar) plates were streaked with the fungus *Candida albicans*. Compound moistened (10 mg/mL compound in DMSO) 7 mm filter paper disks were placed on each streaked plate, and the plates were either kept in the dark in an incubator overnight, placed in room light for 15 minutes and then in the incubator overnight, or left on the benchtop in room light overnight. Three control disks containing DMSO were run along side the disks moistened with compound. Experiments were performed in triplicate using compounds 1A, 1B, 1F, 1H and 1L.

No growth inhibition was observed for the DMSO control disks under any conditions tested. Compounds kept in the dark did not inhibit fungus growth under these experimental conditions. Results indicated that compound 1F produced a zone of inhibition of 7.5 mm when exposed to light for 24 hours. Dye 1B produced a zone of inhibition of 9 mm, and compounds 1A, 1H, and 1L produced a zone of inhibition of 7.5 mm after exposure to light for 15 minutes. For compounds exposed to light overnight, compounds 1B and 1H produced zones of inhibition of 9 mm, compound 1A produced a zone of inhibition of 8 mm, and compound 1L a zone of inhibition of 7.5 mm. Thus, the experiments indicate that the compounds of the present invention inhibit the growth of fungi.

It will be appreciated by those skilled in the art that the method of the present invention will make it possible to inhibit microorganism growth in virus-laden, bacteria-laden, or fungi-laden fluids, surfaces, products, or materials.

Other viruses, bacteria, and fungi can be similarly tested using the methods of this invention without undue experimentation.

It will be readily understood by those skilled in the art that the foregoing description has been for purposes of illustration only and that a variety of embodiments can be envisioned without departing from the scope of the invention. Therefore, it is intended that the invention not be limited except by the claims.

What is claimed is:

1. A method for limiting growth of a microorganism comprising:

exposing a microorganism to an effective amount of a composition comprising a metal-containing compound having the following chemical structure:

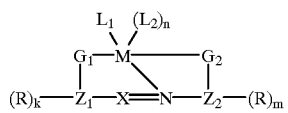

wherein:
Z1 and Z2 each independently represent an arene nucleus, having from 5 to 14 ring atoms;
G1 and G2 each independently represent a metal ligating group, wherein G1 and G2 may be contained within or pendant from at least one of Z1 and Z2;
R represents a hydrogen atom, a halogen atom, an alkyl group, an acylamino group, an alkoxy group, a sulfonamido group, an aryl group, a thiol group, an alkylthio group, an arylthio group, an alkylamino group, an arylamino group, an amino group, an alkoxycarbonyl group, an acyloxy group, a nitro group, a cyano group, an alkylsulfonyl group, an arylsulfonyl group, an alkylsulfoxyl group, an arylsulfoxyl group, an aryloxy group, a hydroxyl group, a thioamido group, a carbamoyl group, a sulfamoyl group, a formyl group, an acyl group, a ureido group, an aryloxycarbonyl group, a silyl group, or a sulfoalkoxy group;
L1 represents a nitrogen heterocycle, substituted with R1 or R2 or both R1 and R2;
R1 and R2 each independently represent a hydrogen, a halogen atom, an alkyl group, including vinyl groups, hydroxyalkyl groups, an acylamino group, an alkoxy group, a sulfonamido group, an aryl group, an alkylthio group, an alkylamino group, an alkoxycarbonyl group, an acyloxy group, an alylsulfonyl group, an alkylsulfoxyl group, an alkylcarbamoyl group, an alkylsulfamoyl group, a formyl group, an acyl group, a silyl group, or a sulfoalkoxy group;
L2 represents a monodentate or polydentate ligand;
X represents nitrogen or a methine (CH) group;
M is selected from the group consisting of platinum and palladium; and
k, m, and n are whole numbers less than or equal to 3.

2. The method of claim 1 wherein the method further comprises exposing the composition to light for at least one time.

3. The method of claim 1 wherein the metal-containing compound is compound 1

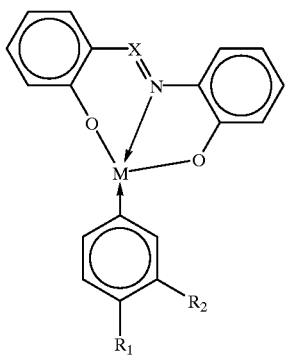

4. The method of claim 3 wherein the metal-containing compound is selected from the group consisting of compound 5

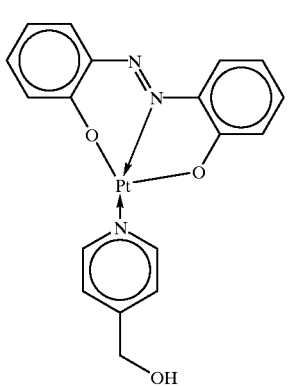

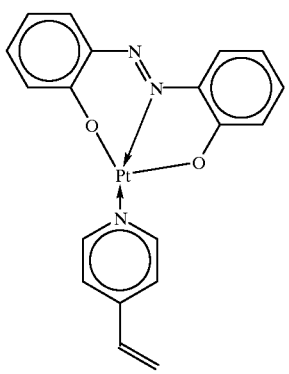

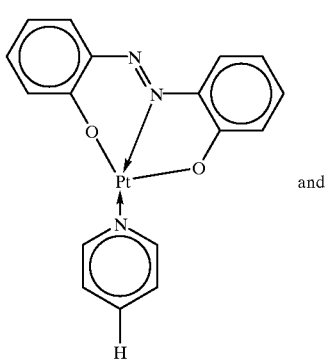

and

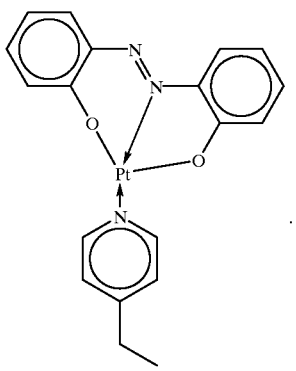

1F

5. The method of claim 1 wherein the microorganism is a virus.

6. The method of claim 5 wherein the virus is an enveloped virus.

7. The method of claim 6 wherein the virus is HIV.

8. The method of claim 6 wherein the virus is a member of the Herpesvirus group.

9. The method of claim 6 wherein the virus is an Influenza virus.

10. The method of claim 1 wherein the microorganism is a bacterium.

11. The method of claim 10 wherein the bacterium is a gram-positive bacterium.

12. The method of claim 10 wherein the bacterium is a gram-negative bacterium.

13. The method of claim 1 wherein the microorganism is a fungus.

14. The method of claim 13 wherein the fungus is a yeast.

15. The method of claim 1 wherein exposing further comprises contacting a surface with the composition.

16. The method of claim 1 wherein the composition comprises the metal-containing compound in a liquid.

17. The method of claim 1 wherein the composition is added to a liquid.

18. The method of claim 1 wherein exposing further comprises adding the metal-containing compound to a solid.

19. The method of claim 1 wherein replication of the microorganism is inhibited by exposing the microorganism to the effective amount of the composition.

20. The method of claim 1 wherein the microorganism is killed by exposing the microorganism to the effective amount of the composition.

21. The method of claim 15 wherein the metal-containing compound on the surface is exposed to light more than once.

22. The method of claim 16 wherein the liquid is exposed to light more than once.

23. The method of claim 17 wherein the liquid is exposed to light more than once.

24. The method of claim 18 wherein the metal-containing compound is exposed to light more than once.

25. The method of claim 1 wherein the composition is in a liquid during the exposing step.

26. The method of claim 1 wherein the composition is a solid during exposing of the microorganism to the effective amount of the composition.

27. The method of claim 1 wherein the composition further comprises at least one other antimicrobial compound.

28. The method of claim 1 wherein n is a whole number less than or equal to 2.

29. The method of claim 1 wherein the alkyl group of $R^1$ and $R^2$ has less than 8 carbons.

30. A method for disinfecting a surface comprising:

applying a composition comprising a metal-containing compound to a surface, the metal-containing compound having the general structure:

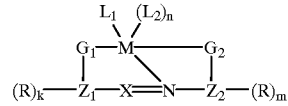

wherein:

Z1 and Z2 each independently represent an arene nucleus, having from 5 to 14 ring atoms;

G1 and G2 each independently represent a metal ligating group, wherein G1 and G2 may be contained within or pendant from at least one of Z1 and Z2;

R represents a hydrogen atom, a halogen atom, an alkyl group, an acylamino group, an alkoxy group, a sulfonamido group, an aryl group, a thiol group, an alkylthio group, an arylthio group, an alkylamino group, an arylamino group, an amino group, an alkoxycarbonyl group, an acyloxy group, a nitro group, a cyano group, an alkylsulfonyl group, an arylsulfonyl group, an alkylsulfoxyl group, an arylsulfoxyl group, an aryloxyl group, a hydroxyl group, a thioamido group, a carbamoyl group, a sulfamoyl group, a formyl group, an acyl group, a ureido group, an aryloxycarbonyl group, a silyl group, or a sulfoalkoxy group;

L1 represents a nitrogen heterocycle, substituted with R1 or R2 or both R1 and R2;

R1 and R2 each independently represent a hydrogen, a halogen atom, an alkyl group, including vinyl groups, hydroxyalkyl groups, an acylamino group, an alkoxy group, a sulfonamido group, an aryl group, an alkylthio group, an alkylamino group, an alkoxycarbonyl group, an acyloxy group, an alylsulfonyl group, an alkylsulfoxyl group, an alkylcarbamoyl group, an alkylsulfamoyl group, a formyl group, an acyl group, a silyl group, or a sulfoalkoxy group;

L2 represents a monodentate or polydentate ligand;

X represents nitrogen or a methine (CH) group;

M is selected from the group consisting of platinum and palladium;

and k, m, and n are whole numbers less than or equal to 3.

31. The method of claim 30 further comprising exposing the surface to light.

32. The method of claim 31 wherein the composition further comprises a second antimicrobial agent.

33. The method of claim 32 wherein the second antimicrobial agent is selected from the group consisting of an antiviral agent, an antibacterial agent and an antifungal agent.

34. A method for limiting the growth of a virus, bacterium and/or a fungus comprising:

contacting the virus, bacterium or fungus with a composition comprising a metal-containing compound having the following formula:

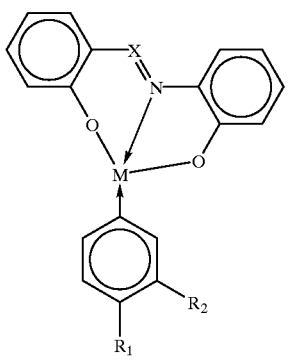

wherein R1 and R2 are each independently selected from the group consisting of H, $CH_2OH$, $CH=CH_2$ and $CH_2CH_3$, X is a methine (CH) group, and M is Pt.

35. The method of claim 34 wherein at least one of R1 or R2 is H.

36. A metal-containing compound having the general structure:

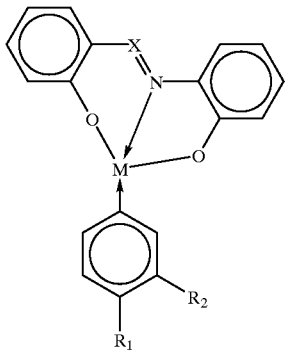

wherein R1 is $CH_2OH$ [or $CH_2CH_3$], R2 is H, [Z] X ia a methine (CH) group, and M is Pt.

37. A method for limiting growth of a microorganism comprising:

exposing a microorganism to am effective amount of a composition comprising a metal-containing compound having a chemical structure of compound 1:

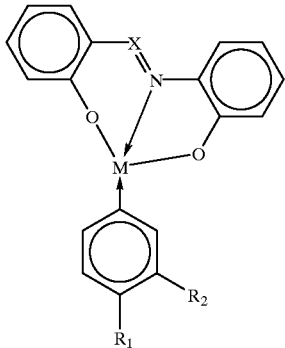

wherein:
R1 and R2 each independently represent a hydrogen, a halogen atom, an alkyl group, including vinyl groups, hydroxyalkyl groups, an acylamino group, an alkoxy group, a sulfonamido group, an aryl group, an alkylthio group, an alkylamino group, an alkocycarbonyl group, an acyloxy group, an alylsulfonyl group, an alkylsulfoxyl group, an alkylcarbamoyl group, an alkylsulfamoul group, a formyl group, an acyl group, a silyl group, or a sulfoalkoxy group;
X represents nitrogen or a methine (CH) group; and
M is a divalent or polyvalent transition metal ion where the coordination number is at least 4.

38. A method for limiting growth of a virus comprising:

exposing a microorganism to an effective amount of a composition comprising a metal-containing compound having the following chemical structure:

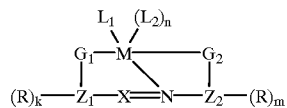

wherein:
Z1 and Z2 each independently represent an arene nucleus, having from 5 to 14 ring atoms;
G1 and G2 each independently represent a metal ligating group, wherein G1 and G2 may be contained within or pendant from at least one of Z1 and Z2.
R represents a hydrogen atom, a halogen atom, an alkyl group, an acylamino group, an alkoxy group, a sulfonamido group, an aryl group, a thiol group, an alkylthio group, an arylthio group, an alkylamino group, an arylamino group, an amino group, an alkoxycarbonyl group, an acyloxy group, a notro group, a cyano group, an alkylsulfonyl group, an arylsulfonyl group, an alkylsulfoxyl group, an arylsulfoxyl group, an aryloxyl group, a hydroxyl group, a thioamido group, a carbamoyl group, a sulfamoyl group, a formyl group, an acyl group, a ureido group an aryloxycarbonyl group, a silyl group, or a sulfoalkoxy group;
L1 represints a nitrogen heterocycle, substituted with R1 or R2 or both R1 and R2;
R1 and R2 each independently represent a hydrogen, a halogen atom, an alkyl group, including vinyl groups, hydroxyalkyl groups, an acylamino group, an alkoxy group, a sufonamido group, an aryl group, an alkylthio group, an alkylamino group, an alkoxycarbonyl group, an acyloxy group, an alylsulfonyl group, an alkylsulfoxyl group, an alkylcarbamoyl group, an alkylsulfamoyl group, a formyl group, an acyl group, a silyl group, or a sulfoalkoxy group;
L2 represints a monodentate or polydenatee ligand;
X represents nitrogen or methine (CH) group;
M is a divalent or polyvalent transition metal ion where the coordination number is at least 4; and
k, m, and n are whole numbers less than or equal to 3.

39. The method of claim 38 wherein the virus is an enveloped virus.

40. The method of claim 39 wherein the virus is HIV.

41. The method of claim 39 wherein the virus is a member of the Herpesvirus group.

42. The metod of claim 39 wherein the virus is an Influenza virus.

* * * * *

UNITED STATES PATENT AND TRADEMARK OFFICE
CERTIFICATE OF CORRECTION

PATENT NO. : 6,248,733 B1
DATED : June 19, 2001
INVENTOR(S) : Landgrebe et al.

It is certified that error appears in the above-identified patent and that said Letters Patent is hereby corrected as shown below:

Column 4,
Line 50, please delete "alylsulfonyl" and insert -- alkylsulfonyl -- therefor.

Column 7,
Line 18, please delete "alylsulfonyl" and insert -- alkylsulfonyl -- therefor.

Column 8,
Line 2, please delete "alylsulfonyl" and insert -- alkylsulfonyl -- therefor.
The structure starting on line 21, please
delete "      and insert --       therefor.

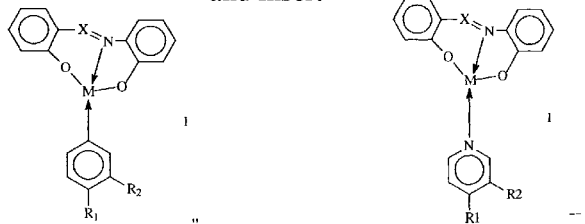

The structure starting on line 44, please
delete "      and insert --       therefor.

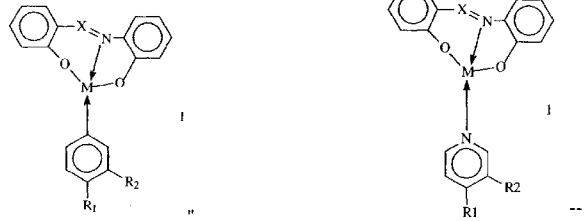

Column 10
Line 50, please delete "alylsulfonyl" and insert -- alkylsulfonyl -- therefor.

Column 11,
The structure starting on line 9, please
delete "      and insert --       therefor.

UNITED STATES PATENT AND TRADEMARK OFFICE
CERTIFICATE OF CORRECTION

PATENT NO. : 6,248,733 B1
DATED : June 19, 2001
INVENTOR(S) : Landgrebe et al.

It is certified that error appears in the above-identified patent and that said Letters Patent is hereby corrected as shown below:

Column 15,
Line 43, please delete "tetraclhloroplatinate" and insert -- tetrachloroplatinate -- therefor.

Column 17,
The structure starting on line 27, please delete " and insert --  therefor.

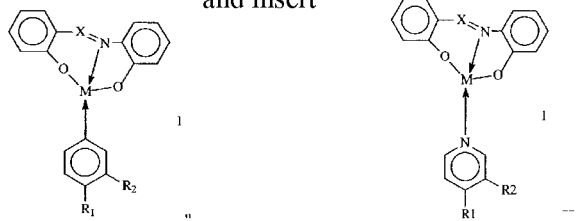

Column 24,
Line 64, please insert -- production -- after "reduced".

Column 25,
Lines 36-37, please delete "quantitate" and insert -- quantitated -- therefor.

Column 31,
Line 53, please delete "alylsulfonyl" and insert -- alkylsulfonyl -- therefor.

Column 32,
The structure starting on line 1, please delete " and insert --  therefor.

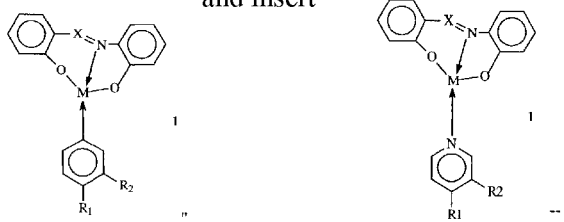

Lines 19-20, please delete "compound 5" and insert -- compounds -- therefor.

Column 33,
Line 57, please delete "mctal-containing" and insert -- metal-containing -- therefor.
Line 60, please delete "the" occurring after "a liquid during".
Line 60, please delete "step" and insert -- of the microorganism to the effective amount of the composition -- therefor.

UNITED STATES PATENT AND TRADEMARK OFFICE
CERTIFICATE OF CORRECTION

PATENT NO. : 6,248,733 B1
DATED : June 19, 2001
INVENTOR(S) : Landgrebe et al.

It is certified that error appears in the above-identified patent and that said Letters Patent is hereby corrected as shown below:

Column 34,
Line 44, please delete "alylsulfonyl" and insert -- alkylsulfonyl -- therefor.

Column 35,
The structure starting on line 1, please delete "        " and insert --        -- therefor.

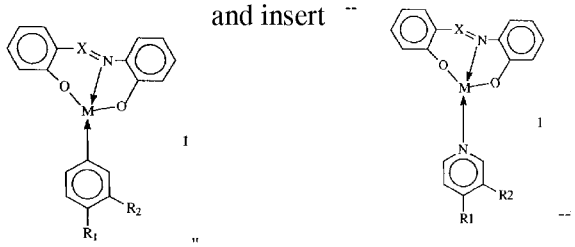

The structure starting on line 26, please delete "        " and insert --        -- therefor.

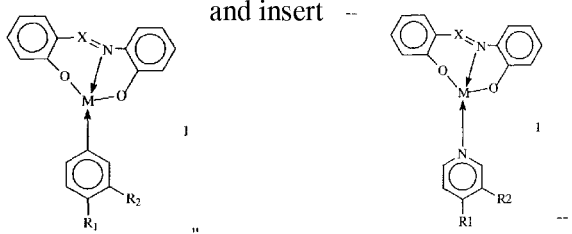

Line 43, please delete "[or $CH_2CH_3$]".
Line 43, please delete "[Z]".
Line 43, please delete "ia" and insert -- is -- therefor.
Line 47, please delete "am" occurring before "effective amount" and insert -- an -- therefor.

Signed and Sealed this

Eighth Day of October, 2002

*Attest:*

*Attesting Officer*

JAMES E. ROGAN
*Director of the United States Patent and Trademark Office*